United States Patent
Nath et al.

(10) Patent No.: US 7,431,467 B2
(45) Date of Patent: Oct. 7, 2008

(54) PORTABLE FORENSIC LIGHTING DEVICE

(75) Inventors: Günther Nath, Otto-Heilmann-Sttrasse 3, 82031 Grünwald (DE); Klaus T. Dünkel, Grünwald (DE)

(73) Assignee: Gunther Nath, Grunwald (DE)

( * ) Notice: Subject to any disclaimer, the term of this patent is extended or adjusted under 35 U.S.C. 154(b) by 283 days.

(21) Appl. No.: 11/020,122

(22) Filed: Dec. 27, 2004

(65) Prior Publication Data
US 2005/0254237 A1    Nov. 17, 2005

(30) Foreign Application Priority Data
May 13, 2004   (DE)   ......................... 10 2004 023 808

(51) Int. Cl.
*F21V 19/04*    (2006.01)
*F21V 7/04*     (2006.01)

(52) U.S. Cl. .......................... 362/20; 362/551; 362/293; 362/294

(58) Field of Classification Search ................. 362/551, 362/198–199, 293–294, 580–581
See application file for complete search history.

(56) References Cited

U.S. PATENT DOCUMENTS

| | | | |
|---|---|---|---|
| 4,633,128 A * | 12/1986 | Roberts et al. | ............... 313/113 |
| 4,933,816 A * | 6/1990 | Hug et al. | ................... 362/551 |
| 5,072,338 A | 12/1991 | Hug et al. | |
| 5,306,642 A | 4/1994 | Reagen et al. | |
| 5,515,162 A | 5/1996 | Vezard et al. | |
| 5,734,229 A * | 3/1998 | Bavaro et al. | .................. 315/86 |
| 5,746,495 A | 5/1998 | Klamm | |
| 5,832,159 A * | 11/1998 | Davis | ........................... 385/53 |
| 5,997,165 A | 12/1999 | Lehrer | |
| 6,646,379 B1 * | 11/2003 | Nohara et al. | ................ 313/623 |
| 6,831,414 B2 * | 12/2004 | Van Erk et al. | ............. 313/623 |
| 6,927,539 B2 * | 8/2005 | Arimoto et al. | ................ 315/59 |
| 7,195,388 B2 * | 3/2007 | Hori | ........................... 362/583 |
| 2005/0129108 A1 * | 6/2005 | Bendall et al. | .......... 375/240.01 |
| 2006/0050525 A1 * | 3/2006 | Verrier et al. | ................ 362/551 |

FOREIGN PATENT DOCUMENTS

GB    2 340 926 A    1/2000
WO    WO98/45645 A1    10/1998

* cited by examiner

*Primary Examiner*—Ali Alavi
(74) *Attorney, Agent, or Firm*—Barnes & Thornburg LLP

(57) ABSTRACT

Crime scene lighting devices are used in forensic criminology for illumination and investigation at crime scenes using fluorescence excitation. High radiation powers are required both for white light in the so-called general search and for the criminologically relevant UVA-blue-green range. Moreover, it should be possible for the crime scene investigator to use the forensic lighting device portably and independent from the public power supply. The present disclosure relates to a suitable crime scene light device with a mercury ultra high pressure lamp as the light source, a light guide and terminals for operating the lamp selectively with an accumulator or the public power supply system. A suitable carrier bag, a so-called lorgnette with various longpass filters and a cross-section converter for visualizing shoeprints form useful accessories of the forensic lighting device.

22 Claims, 6 Drawing Sheets

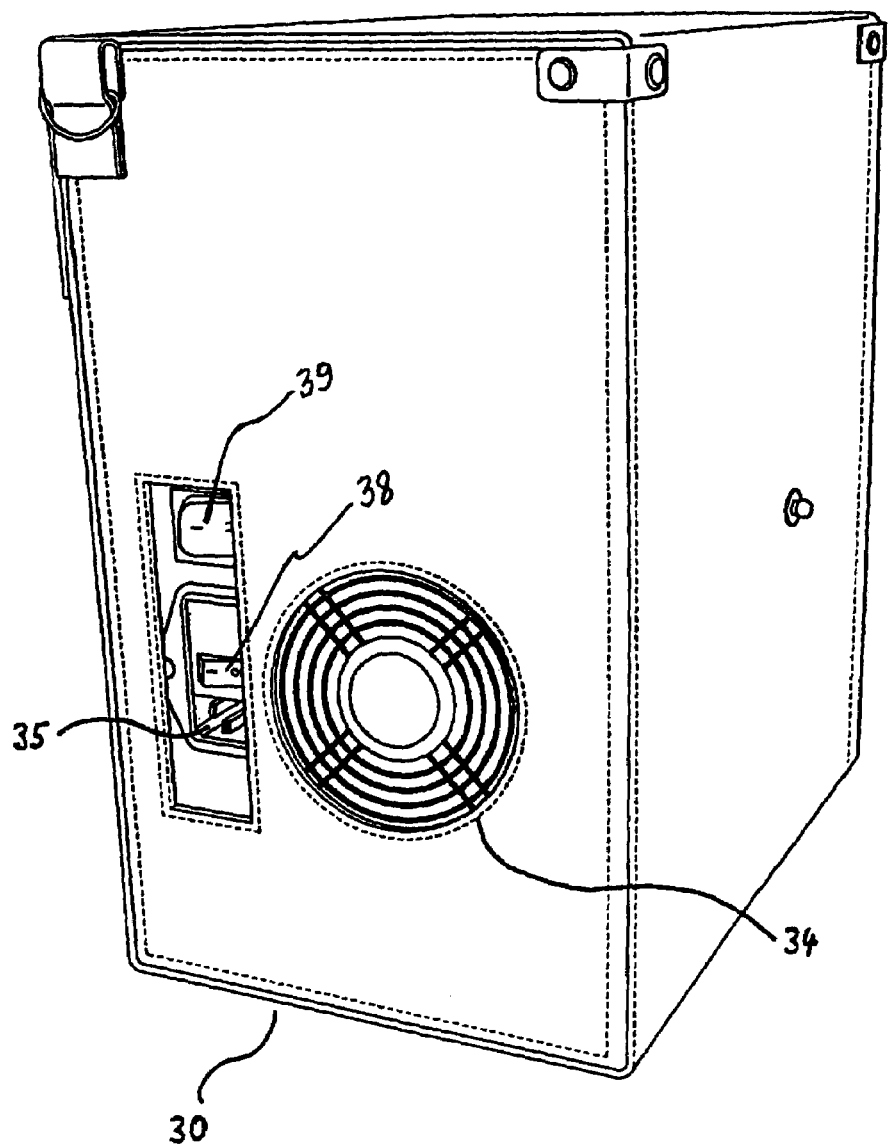

PORTABLE FORENSIC LIGHTING DEVICE

CROSS-REFERENCE

This application claims priority to German Patent Application 10 2004 023 808.1 filed on May 13, 2004, whose disclosure is incorporated herein by reference.

BACKGROUND

The present disclosure relates to a portable forensic light source device for mobile use at a crime scene.

In forensic criminology, so-called forensic lighting devices are used for crime scene investigation. They do not only serve for illumination of poorly lit crime scenes but also for visualizing evidence traces, such as hair, body fluids or fingerprints, at the crime scene by means of fluorescent effects.

For this latter use, forensic lighting devices are required to be capable of emitting not only intense white light but also light of particular spectral regions within the range of 300-700 nm wavelength with sufficiently high emission power, such that fluorescent effects may be observed also at daylight. The so-called forensic range of use comprises the frequency range useful for crime scene investigation and ranges from ultraviolet light (UVA-light) of a wavelength of circa 300 nm up to the long wave limit of visible light at a wavelength of circa 700 nm. Here the bands UVA (320-400 nm), Blue (400-500 nm) and Green (500-560 nm) are of particular importance, as they are used for exciting fluorescence of traces, often in connection with coloring methods. The long wave fluorescence emission caused by the Stokes shift is observed through observation glasses equipped with longpass filter lenses blocking short wave excitement emission.

For allowing the light sources to be used as mobile and flexible as possible, it is desired to operate them with an accumulator independent from the line current. In order to improve the handling at the scene, forensic lighting devices further comprise liquid core light guides attached to the light source device guiding the light from the light source inside the device to the light output in the hand of the user.

In order to make shoeprints visible, so-called beam cross-section converters are often used. These are usually formed by a one-sided linearly expanded bundle of optical fibers operating as a flexible light guide from the light source to the floor where light is emitted tangentially onto a wider area, such that shoeprints may be detected more readily.

Xenon super high pressure lamps of sufficiently high electrical power (300 to 500 W) offer a high illumination power continuously over the visible as well as over the non-visible spectral range. However, two thirds of the emission energy are in the near infrared range and therefore outside the forensic range of use. As a high power supply is required due to the low level of efficiency, it has to be provided by the power supply system or a particularly powerful and hence heavy accumulator. The resulting heavy weight of the crime scene light source including the accumulator would amount to more than 30 kg, such that the device would be bulky and too heavy to carry. Consequently, xenon forensic lighting devices in this power range (300-500 W) are not available at all with accumulators. Moreover, the high infrared portion of the emitted light results in an excessive heating of the filter and the liquid core light guide, thereby shortening the light guide's lifetime. Furthermore, the strong heat generation requires the use of light guides with relatively large light-active diameters (8 to 10 mm). This limits flexibility and ease of use. Xenon lamps with less power (e.g. circa 35 W) do not suffer from the above mentioned disadvantages, but exhibit an emission power in the range of use which, in particular in the near UVA range, is much too poor, such that at daylight crime scene investigation by fluorescence excitation becomes impossible.

Mercury super high pressure lamps such as the Osram HBO lamp with a mercury pressure of less than approx. $10^7$ Pa (ca. 100 atm) exhibit a pronounced line spectrum. Due to the lack of a continuous spectral background between the spectral lines in the range of wavelengths between 300 and 700 nm, the possibility of selecting particular spectral windows is strongly restricted, as it is basically confined to the position of the spectral lines of mercury. Moreover, the long heating time after switching on the forensic lighting device (some minutes) exclude a quick availability.

Tungsten halogen lamps emit 90% of their radiation within the infrared range, whereas the UVA portion is negligibly small. Therefore, the efficiency is even smaller than that of xenon lamps. While operation with an accumulator is possible up to a power of 150 W, the available radiation in the important range of UVA, blue and green is extremely small.

SUMMARY

An aspect of the present disclosure is to overcome the above-mentioned disadvantages and to provide a mobile forensic lighting device which, when used at the crime scene, can easily be carried by the user and which offers a sufficient radiation power in the whole forensic range of use.

A portable lighting device is proposed, which is suitable for mobile use at a crime scene, wherein the lighting device includes a light source and a light guide with a light output end for guiding light from the light source to the light output end. The lighting device further comprises a terminal, shown as numerical designation 35 in FIG. 3b, for power supply of the light source from the public power supply system and another terminal, shown as an upside down T-shaped element 37 above LED display 16 at FIG. 1, for power supply of the light source by battery power such that the lighting device may be operated selectively by switches 38 and 39, as shown in FIG. 3b, with power from the power supply system or a battery. The light source of the lighting device is a mercury ultra high pressure lamp.

The mercury ultra high pressure lamp of the forensic lighting device has a radiation spectrum, which covers the forensic range of use particularly well. Due to the high pressure in the mercury ultra high pressure lamp (in the range of $2\times10^7$ Pa or 200 atm), an additional strong continuous background spectrum is generated by the broadening of spectral lines from the line spectrum as observed generally for mercury lamps. This allows for a flexible selection of spectral windows for crime scene investigation. The underlying line spectrum of the mercury ultra high pressure lamp is well-suited, since the light guide provides particularly high emission powers within important forensic spectral ranges such as e.g. UVA (365 nm), violet (406 nm) or green (548 nm).

Due to the low radiation power in the infrared range, which is irrelevant for forensic analysis, the mercury ultra high pressure lamp is characterized by a high degree of efficiency in the forensic range of use, i.e. for crime scene illumination and investigation purposes. Accordingly, the required electrical power of the forensic lighting device is low, such that besides operating the forensic lighting device from the power grid, it may also be operated with a relatively light accumulator. Consequently, the forensic lighting device may indeed be carried easily by the user.

A further advantage is due to the fact that the forensic lighting device is readily usable because of the short heating time of only 20-30 seconds for the mercury ultra high pressure lamp.

Further advantageous aspects of the disclosure concern in particular: a filter disc operable from outside and allowing for a quick change of bandpass filters; a telescopic single-bar stand secured against rotational movements and adapted to fix a handpiece, which is connected via the light guide to the lamp device; and a carrier bag, inside of which the forensic lighting device may be operated and equipment (goggles, charging device, light guide, cross-section converter, lorgnette etc.) be stored. The carrier bag further comprises openings for cooling the lighting device.

Other aspects of the lighting device will become apparent from the following description when considered in conjunction with the accompanying drawings.

BRIEF DESCRIPTION OF THE DRAWINGS

FIG. 3b is a rear-side view of the device in the carrier bag.

DETAILED DESCRIPTION OF THE DRAWINGS

Figure 1:
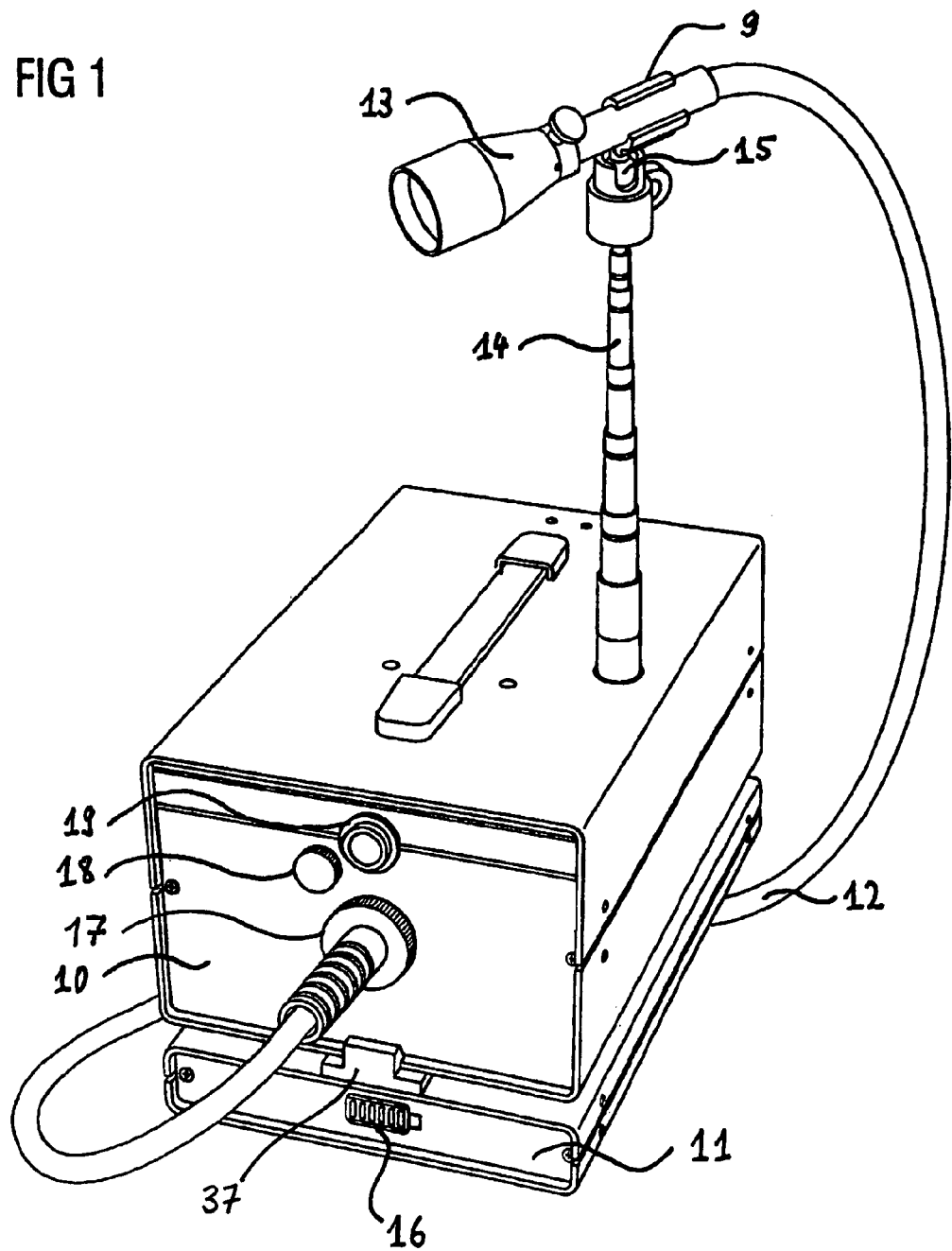
FIG. 1 is a perspective view on the forensic lighting device according to the present disclosure.

FIG. 1 displays the exterior assembly of the forensic lighting device according to the present disclosure with the flanged accumulator package 11 and, coupled to the lighting device, the liquid core light guide 12, Series 300 by Lumatec, φ 5 mm, length 1500 mm, including the attached beam collimator 13. In addition to the terminal for the collimator 13 with two $SiO_2$ lenses, the handpiece at the end of the liquid core light guide comprises a hand-switch (shown in FIGS. 6a and 6b) for operating a shutter. The liquid core light guide 12 is fixed by a holding clip 9 on a non-rotatable telescopic single-bar stand 14, wherein the holding clip 9 is mounted on a fixable ball-shaped head 15, such that the light beam may be directed in any direction for photographical documentation. The telescopic single-bar stand 14 is fixedly connected to the lamp housing 10, such that the forensic lighting device itself forms the basis for the stand.

The accumulator power package 11 including lithium ion or lithium polymer cells is flanged to the lamp housing 10 but is essentially spaced apart therefrom at a distance of approximately 1 cm, thereby forming the standing for the lighting device. Alternatively, the cells of the accumulator may be nickel-cadmium or metal hydride cells. Fresh air for the cooling fan is suctioned through the slit between accumulator package 11 and lamp housing 10 defined by the rubber feet of the lamp housing 10. In addition to their mechanic coupling, the accumulator package 11 is also coupled electrically to the device part, namely via a 8-pole plug represented by a terminal 37 in FIG. 1. The 8-pole plug accomplishes the serial connection of four sub-units of the lithium ion battery package 11 in the plugged state, such that in the unplugged state the accumulator package comprises four decoupled battery sub-units. This is prescribed for the shipping of combined lithium ion batteries having a total capacity of 6.5 Ah as in the present case. The charging state of one of the four battery sub-units (six cells arranged in two serially connected groups, each group comprising three parallely connected cells) may be read off from outside on an LED display 16 on the accumulator package 11. The lamp housing may also be operated with alternating current from the public power supply system separately from the accumulator package 11, the connection to the public power supply system shown as a terminal or plug 35 in FIG. 3b.

Figure 2:
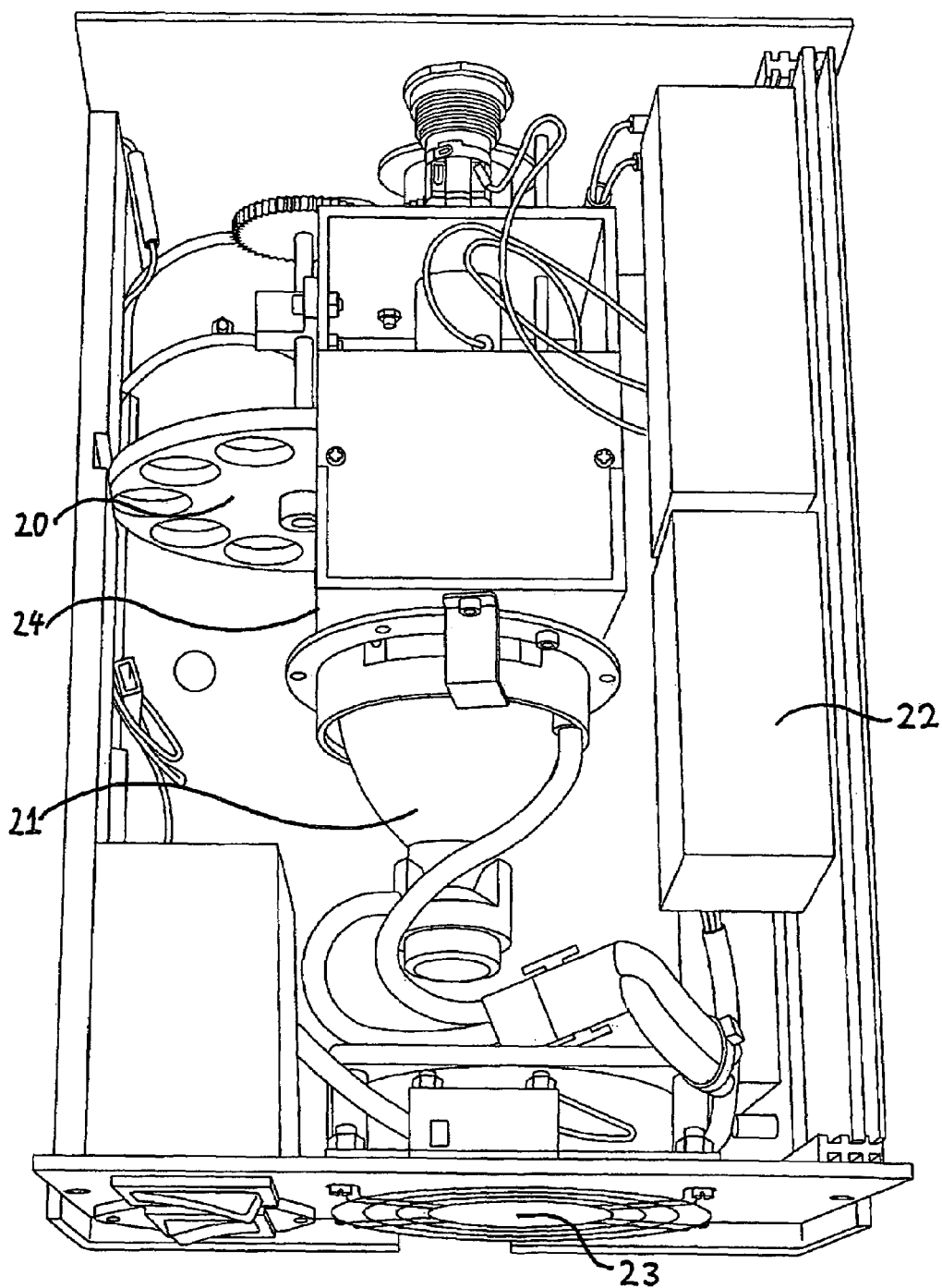
FIG. 2 is a cross-sectional view of the device.

As shown in FIG. 2, a filter disc 20 including in total 10 to 12 rounded band-pass filters is located inside the lamp housing 10. This filter disc 20 may be rotated manually by a thumb wheel 17, wherein each filter configuration is defined by engagement of the thumb wheel. Possible filter configurations are:

| | |
|---|---|
| UVA (320-400 nm) | general search |
| White (400-700 nm) | general search |
| UVA + Blue (320-500 nm) | general search |
| Blue (400-500 nm) | general search |
| Violet (395-435 nm) | |
| longwave blue (450-500 nm) | |
| Turquoise (485-525 nm) | |
| Green (510-550 nm) | |
| Green (540-570 nm) | |
| Orange (570-610 nm) | |
| Red (600-640 nm) | |
| Red (630-670 nm) | |

Furthermore, the front panel comprises a manually operable intensity control 18 and a push-button 19 for operating a shutter.

FIG. 2 shows the optical arrangement inside the lamp housing 10. The mercury ultra high pressure lamp itself, for example an UHP lamp by Philips or a VIP lamp by OSRAM, as used in modern video beamers, is located inside a dielectrically coated ellipsoid reflector 21. The mercury plasma of the lamp is located in a first focal point of the reflector and the light entrance aperture for the light guide 12 in the second focal point. The coating layer inside the reflector 21 is composed of $TiO_2$ or $SiO_2$ or of $TaO/SiO_2$. The substrate is an ellipsoid-shaped mold glass cap. For the interior of the cap, a coating with a high refraction in the spectral range of 320-700 nm and higher transmission for wavelengths>700 nm is chosen. Preferred coatings are those containing the materials tantal oxide (for the highly refractive layer) and $SiO_2$ (for the low refractive layer). Alternatively, a broadband metallic reflective coating is applied on the reflector, e.g. a broadband high reflective layer (nearly 100% reflection at wavelengths of 320-700 nm) essentially containing aluminum. Preferably, the aluminum layer is provided with a $SiO_2$ protection layer. Preferably, the inner pressure of the lamp is higher than $1.4 \times 10^7$ Pa, more preferably approximately $2 \times 10^7$ Pa (200 atm). The distance between the lamp electrodes is typically less than 2 mm.

The power of the mercury ultra high pressure lamp ranges from 80 W to 250 W, preferably from 80 W to 140 W and more preferably from 100 W to 120 W. In particular, the lighting device has an output power of approximately 1.5 W in the range of wavelengths between 320 nm and 400 nm, at least 3 W in the range of 400 nm and 500 nm, at least 2 W in the range of 500 nm to 600 nm and at least 6 W in the range of 400 nm to 700 nm, when measured at the output of a flexible liquid core light guide having a light active diameter of 5 mm and a length of approximately 150 cm.

The reflector 21 is fixedly mounted on a U-shaped metallic angular module 24, such that the user may insert or replace the reflector lamps with different coatings easily and in an already pre-adjusted condition.

In the optical path between the lamp reflector 21 and the light entrance surface of the light guide 12, there are disposed a) the filter disc 20; b) the diaphragm of the intensity control 18 and c) the diaphragm of the shutter, which is operated here by a rotary magnet and the push-button 19. In addition, the diaphragm can also be operated by the hand-switch in the handpiece of the liquid core light guide.

Figure 5:
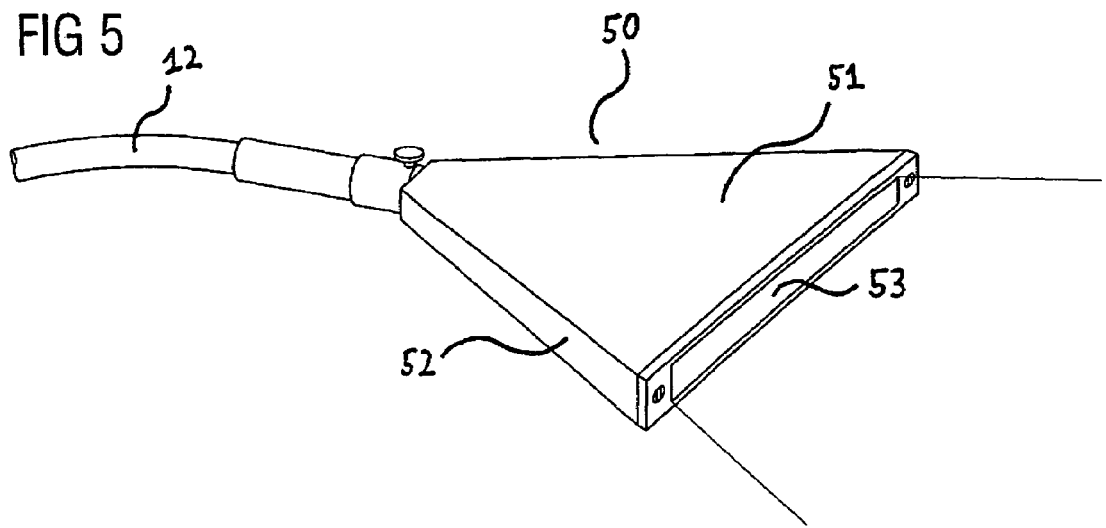
FIG. 5 is a perspective view of the cross-section converter.
Figure 6A:
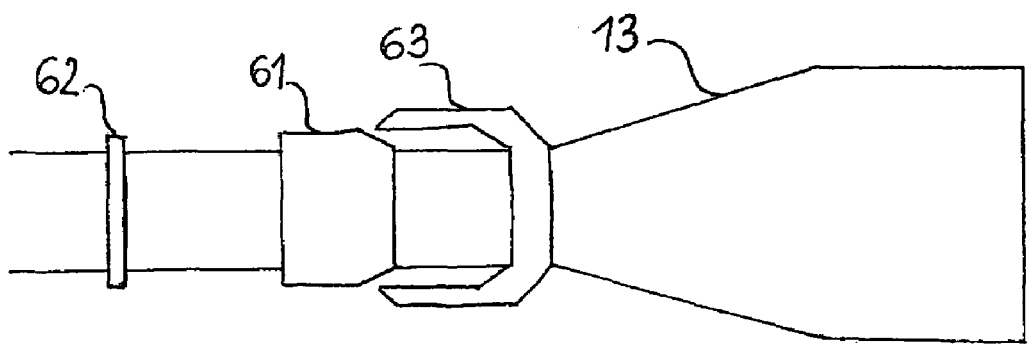
FIG. 6a is a side elevational view of the output end of the light guide with the hand-switch in the unlocked position.
Figure 6B:
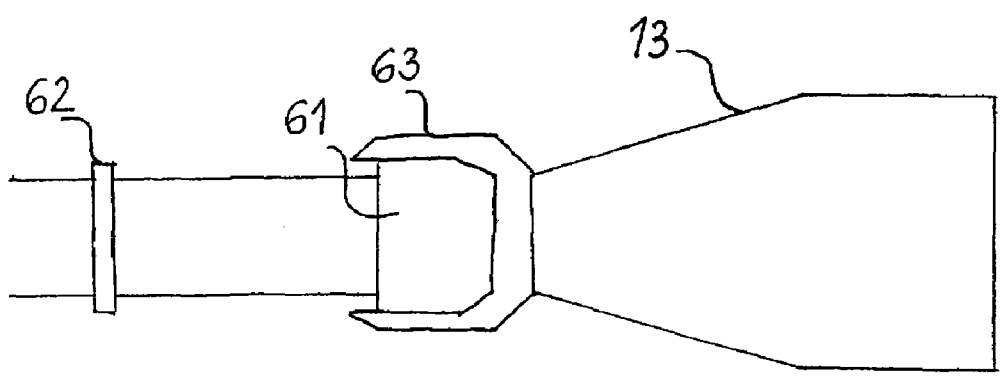
FIG. 6b is a side elevational view of the output end of the light guide with the hand-switch in the locked position.

The hand-switch, which is employed here, is based on the construction displayed in FIG. 5 of the document WO 00/22343, which is incorporated herein by reference. The switch is provided with an additional snapping lock as illustrated in FIGS. 6a and 6b. In its locked state, the snapping lock 63 blocks the hand-switch and thereby prevents unintentional activation of the light beam. Moreover, the hand-switch is electrically coupled with the shutter in the lamp housing 10 via strands arranged inside the protection tube of the liquid core light guide 12.

The hand-switch comprises an annular sleeve 61 surrounding the rotatable handpiece of the liquid core light guide 12 and containing a magnet ring. In the proximal direction of the sleeve 61, a switch for magnetic activation (e.g. a Reed switch) is located inside the handpiece, wherein this switch may be activated by pushing back the sleeve 61 towards and approximating the magnet ring, such that the shutter in the lamp housing is opened and the light beam is activated. The push-back movement of the sleeve 61 is confined by a stopping ring 62 encircling the handpiece. In addition, further accordingly polarized magnet rings inside the handpiece ensure that a spring-like magnetic resisting force needs to be overcome when the sleeve 61 is pushed back and the light beam is thereby activated, and that the sleeve 61 returns and remains in its distal position in the absence of exterior forces. In this position, the Reed switch is inactive and the shutter is closed. Similarly, it is possible to generate the force resisting the push-back movement of the sleeve 61 by mechanical springs inside or outside the handpiece.

In view of the high radiation power of the forensic lighting device, the hand-switch contributes to the operational security of the device. This security is further improved by the snapping lock 63 arranged on the handpiece of the light guide 12, fixing the sleeve 61 in the locked state in its distal position and thereby allowing the hand-switch to be operated only in the unlocked state. Preferably, the snapping lock 63 is embodied by a clamp which holds the sleeve 61 mechanically in the locked state.

The strands arranged inside the light guide tube are connected to annular contacts at the light input end of the light guide 12, which are contacted by spring pins protruding inside the lamp housing 10 radially from the plug-in opening in the interior direction and thereby are coupled electrically with the shutter in the lamp housing 10. Therefore, mounting the light guide 12 to the lamp housing 10 will not only establish the light connection but simultaneously create a reliable and uncomplicated electrical connection of the hand-switch and the shutter. Here, the hand-switch is connected in parallel to the push-button 19, such that the permanent activation of the hand-switch for continuous operation (e.g. in the lab) can be circumvented by a single activation of the push-button 19.

Preferably, the diaphragm of the shutter is positioned between the lamp reflector 21 and the filter disc 20 in order to enhance the lifetime of the filters. Further, a circuit board 22 is arranged inside the lamp housing 10. The board 22 comprises the components of the voltage control, the ignition device of the ultra high pressure lamp and the voltage supply of the ventilator 23 as well as the DC-DC converter. The latter one is activated in accumulator operation and converts the low accumulator voltage of about 33 V to a voltage approximately ten times as high, such that the mercury ultra high pressure lamp may be operated with its own power supply. The fact that the DC-DC converter is generally arranged inside the lamp housing 10 of the lighting device, allows for a later upgrading of the lighting device with the accumulator package 11. The accumulator package is mainly required for work at the crime scene and less important for lab applications.

Due to its high efficiency, i.e. the relation of forensically usable radiation to required electrical power, the use of the mercury ultra high pressure lamp as a forensic lighting device with maximal optical emission power allows for a very compact construction. In particular, the forensic lighting device including accumulator package 11 as shown in FIG. 1 has a dimension of only 165 mm in height, 175 mm in width, 260 mm in length and a weight of 5.3 kg.

This means that the forensic lighting device according to the present disclosure may be hung over the shoulder and carried conveniently in this way. It may even be operated while being disposed inside a carrier bag.

Figure 3A:
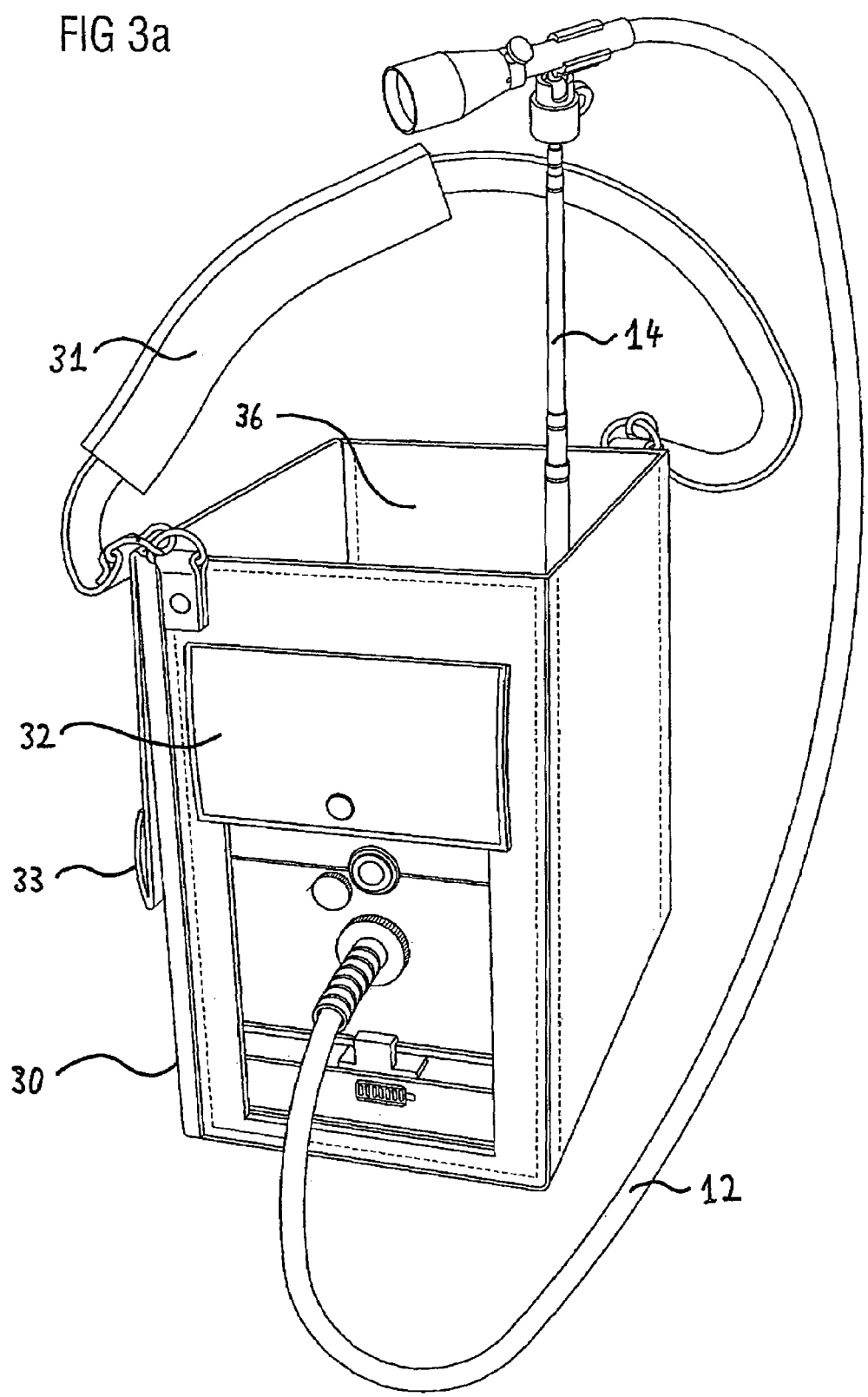
FIG. 3a is a perspective view of the device inside the carrier bag.

FIG. 3a displays the carrier and operating bag 30 particularly designed for the forensic lighting device according to the present disclosure. The bag is made of synthetic leather and provided with carrying straps 31 and closable opening flaps 32, 33 at its front and upper sides. The opening flaps are folded using fixation by snap fasteners and may be closed by Velcro bands. The front flap opening 32 allows the control elements of the lighting device to be operated therethrough and the flexible liquid core light guide 12 to be plugged in. It further allows fresh air to be suctioned in for cooling by the cooling means 23. The air is then blown out again through the circular opening 34 of the bag 30 as shown in FIG. 3b. In addition, the forensic lighting device is further supplied with fresh air through holes disposed on the sides of the bag, ideally in the height of the slit between accumulator package 11 and lamp housing 10 (not shown).

As the operating bag 30 is approximately 130 mm higher than the complete forensic lighting device, it offers further storage space 36 inside and above the device for storing the most important accessories of the forensic lighting device: UV protection goggles, longpass goggles, cross-section converter, liquid core light guide, lorgnette etc. Alternatively, the carrier bag may comprise a side pocket in which the liquid core light guide can be stored separately. Thereby, the light guide can be additionally protected against possible damages. The option of operating the forensic lighting device directly from the carrier bag 30, the latter one also containing the accessories, allows for an immediate and uncomplicated use of the light at the crime scene. This results in a great advantage over conventional forensic lighting devices.

Furthermore, the possibility of immediately fixing the light cone using the telescopic stand 14 built in the device allows for a convenient documentation of traces.

One of the most important accessories of the forensic lighting device consists in a set of longpass filters for observing fluorescence emission of colored or non-colored traces, wherein the longpass filters are supposed to suppress the short wave excitation emission of the forensic lighting device and let the long wave fluorescence emission pass. These longpass filters are usually offered in form of various goggles with different transmission edges.

In order to adjust the optimal contrast of a fluorescent trace, goggles with varying edge wavelength have to be tested, a complicated and time-consuming procedure, in particular in case the crime scene investigator has to wear glasses anyway.

Figure 4:
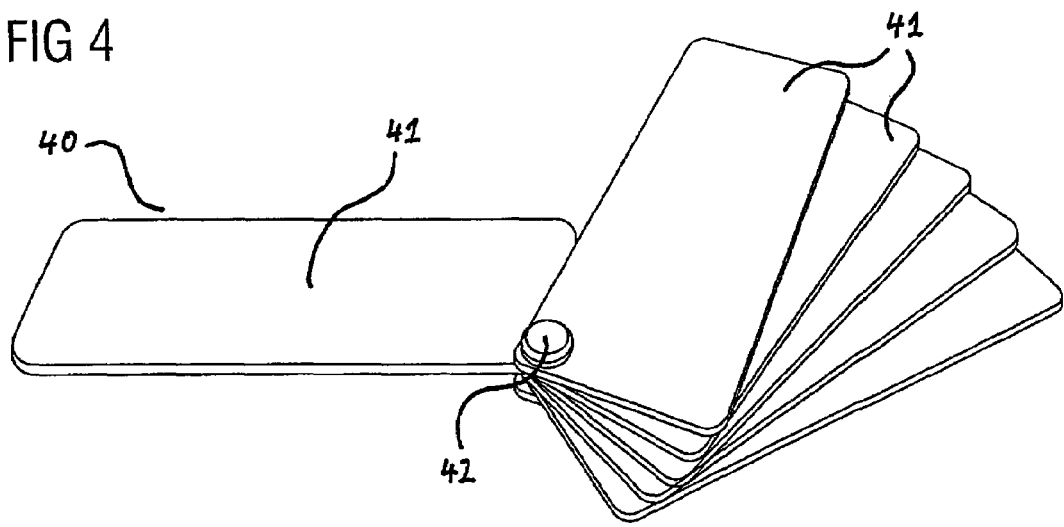
FIG. 4 is a perspective view of the lorgnette.

FIG. 4 displays a longpass filter lorgnette 40 for the forensic lighting device according to the present disclosure, in which a couple of longpass filters are integrated and may be spread out fan-like in one hand, similar to playing cards, such that the observer may quickly select the observation filter with optimal contrast for the fluorescence image. The optimal observation filter can then be used separately by spreading out the lorgnette and holding the desired filter in front of the eyes.

The particular filters 41 preferably consist of colored plastic, in particular plexiglass, comprise a rectangular oblong geometry and are held by an axis 42 in one corner parallely to each other and rotatably with respect to each other. The whole filter assembly is located inside a metallic U-shaped cover (not shown) providing the fixation of the rotary axis 42 on both sides. Typical dimensions of a single filter sheet 41 are 140 mm×50 mm.

A further important accessory of the forensic lighting device is the so-called cross-section converter 50 as shown in FIG. 5.

In cross-section, it has the shape of an isosceles triangle defined by two parallel mirror surfaces 51 spaced apart from each other. These surfaces 51 may be formed as one-sided mirror metal plates, e.g. of aluminum, wherein the mirror surfaces 51 are facing each other. The distance of the triangle plates is defined by side walls 52, which are highly reflecting on their facing interior surfaces as well. The front slit at the basis of the triangle is covered by a transparent window 53 consisting for example of plexiglass. The light output surface of the light guide 12 is coupled at the vertex of the isosceles triangle, such that the total radiation fills the interior space confined by the mirror surfaces. Due to the divergence of the light beam and the multiple reflection on the inner mirror surfaces 51 of the hollow triangle, the beam broadens and exits from the transparent basis surface 53 in expanded form.

Preferably, the triangle surfaces 51 and the side walls 52 consist of aluminum. The high interior reflectivity may be accomplished by electrolyte polishing or gluing of reflecting foils.

It is further possible to replace the hollow triangle with inner highly reflective surfaces by a triangle-shaped plate made of massive plexiglass (or another transparent plastic material such as Makrolon), wherein the inner reflection of light is given by the total reflection at the interface glass/air. At higher light powers (approximately 10 W), the hollow triangle with inner highly reflective surfaces is favourable, as for example plexiglass starts to melt at high beam power densities, which appear in particular close to the site where the light is coupled in.

Although the present disclosure has been described and illustrated in detail, it is to be clearly understood that this is done by way of illustration and example only and is not to be taken by way of limitation. The spirit and scope of the present disclosure are to be limited only by the terms of the appended claims.

We claim:

1. A portable lighting device for mobile use at a crime scene, including:
   a light source;
   a light guide for guiding light from the light source to a light output end of the light guide;
   a first terminal for connecting the light source to a power supply system; and
   a second terminal for connecting the light source to a battery,
   wherein the lighting device may be operated selectively with power from the power supply system or from the battery,
   wherein the light source is a mercury ultra high pressure lamp;
   an accumulator which is connectable to the second terminal of the device and supplying it with battery power; and
   wherein the accumulator is one of a lithium ion accumulator, a lithium polymer accumulator, a nickel-cadmium accumulator and a metal hydride accumulator.

2. The lighting device of claim 1, wherein the inner pressure of the mercury ultra high pressure lamp is higher than $1.4 \times 10^7$ Pa, preferably approximately $2 \times 10^7$ Pa (200 atm).

3. The lighting device of claim 1, wherein the power of the mercury ultra high pressure lamp ranges from 80 W to 250 W, preferably from 80 W to 140 W and more preferably from 100 W to 120 W.

4. The lighting device of claim 3, further comprising a reflector having the shape of an ellipsoid, in which the mercury ultra high pressure lamp is built in, wherein a mercury plasma of the lamp is located in a first focal point of the ellipsoid.

5. The lighting device of claim 4, wherein the interior coating of the reflector is made of a dielectric material or aluminum.

6. The lighting device of claim 4, wherein the interior coating of the reflector comprises a higher light reflection in the wavelength range from 320 nm to 700 nm than in the range above 700 nm.

7. The lighting device of claim 4, wherein the light guide is a liquid core light guide and is connectable to the light source such that a light entrance aperture for the liquid core light guide is located in the second focal point of the ellipsoid.

8. The lighting device of claim 1 including a filter wheel operable by a user from outside by use of a thumb wheel for selecting different ranges of wavelengths between 300 nm and 700 nm by means of corresponding filters.

9. The lighting device of claim 1 having a radiation power of approximately 1.5 W in the range of wavelengths between 320 nm and 400 nm, at least 3 W in the range of 400 nm and 500 nm, at least 2 W in the range of 500 nm to 600 nm and at least 6 W in the range of 400 nm to 700 nm, as measured at the output end of a flexible liquid core light guide having a light active diameter of 5 mm and a length of approximately 150 cm.

10. The lighting device claim 1 including an intensity control for controlling the light intensity.

11. The lighting device claim 1, wherein the light guide includes a liquid core and the light guide comprises a light-active diameter of approximately 5 mm.

12. The lighting device of claim 11, further comprising a beam collimator, which is arranged at the light output end of the liquid core light guide.

13. The lighting device of claim 1, further comprising a hand-switch, in particular a magnetically activated switch at the light output end of the light guide for interrupting the light path between light source and light entrance end of the light guide.

14. The lighting device of claim 13, wherein the hand-switch comprises a snapping lock for blocking the switch in the locked state.

15. The lighting device of claim 1, wherein
   the light source is contained in a lamp housing,
   the light guide and the lamp housing are connected with each other via a plug-and-socket connection;

the interruption of the light path is accomplished by a shutter provided between the light source and the plug-and-socket connection; and the shutter and the hand-switch are electrically connected via strands guided inside the light guide, ring electrodes provided circumferentially at the connector plug of the light guide and sliding contacts engaging in the plug opening of the lamp housing, wherein the sliding contacts are preferably spring pins.

16. The lighting device of claim 1, wherein the light source is contained in a module, which is replaceable as a complete unit, wherein different modules comprise differently coated reflectors.

17. The lighting device of claim 1, wherein the accumulator can be charged selectively with one of DC-voltage of about 12 to 24 V and AC-voltage from the power grid in the range of 90 to 240 V.

18. The lighting device of claim 1, further comprising a fan for cooling the device.

19. The lighting device of claim 1, further comprising a stand mounted to the device with a ball-shaped joint, wherein the stand preferably comprises a axially non-rotatable telescopically extractable bar.

20. The lighting device of claim 1, further comprising a carrier bag for carrying the device while it is in use.

21. The lighting device of claim 1, further comprising a lorgnette with various color filters.

22. The lighting device of claim 1, further comprising a cross-section converter, wherein the cross-section converter comprises two acute-angled triangle-shaped metal plates mounted parallely to each other having side walls at the edges, all interior surfaces except a transparent side wall opposed to the acute-angle end are highly reflective, and the light guide is connectable to the space confined by the highly reflective walls of the cross-section converter at the acute-angle end.

* * * * *